United States Patent
Wang et al.

(10) Patent No.: US 10,654,082 B2
(45) Date of Patent: May 19, 2020

(54) METHOD USING ARTIFICIAL FREEZING TECHNIQUE FOR SEALING AND DISPLACEMENT OF SOIL POLLUTANT

(71) Applicants: China University of Mining and Technology, Jiangsu (CN); CHINA COAL CONSTRUCTION GROUP LIMITED CORPORATION, Beijing (CN)

(72) Inventors: Jianzhou Wang, Jiangsu (CN); Guoqing Zhou, Jiangsu (CN); Jinhong Yang, Beijing (CN); Hengchang Liang, Jiangsu (CN); Jie Yang, Beijing (CN); Tuo Chen, Jiangsu (CN); Guangsi Zhao, Jiangsu (CN); Shuxing Liu, Jiangsu (CN); Fengyuan Jiu, Jiangsu (CN); Heng Zhou, Jiangsu (CN); Haoxuan Zhang, Jiangsu (CN); Dan Song, Jiangsu (CN)

(73) Assignees: China University of Mining and Technology, Jiangsu (CN); CHINA COAL CONTRUCTION GROUP LIMITED CORPORATION, Beijing (CN)

( * ) Notice: Subject to any disclaimer, the term of this patent is extended or adjusted under 35 U.S.C. 154(b) by 0 days.

(21) Appl. No.: 16/462,528

(22) PCT Filed: Dec. 1, 2017

(86) PCT No.: PCT/CN2017/114262
§ 371 (c)(1),
(2) Date: May 20, 2019

(87) PCT Pub. No.: WO2018/126826
PCT Pub. Date: Jul. 12, 2018

(65) Prior Publication Data
US 2019/0275572 A1    Sep. 12, 2019

(30) Foreign Application Priority Data

Jan. 5, 2017 (CN) .......................... 2017 1 0008526

(51) Int. Cl.
*B09C 1/00*        (2006.01)
*B09C 1/06*        (2006.01)
(Continued)

(52) U.S. Cl.
CPC .................. *B09C 1/06* (2013.01); *B09C 1/00* (2013.01); *B09C 1/08* (2013.01); *F25D 17/02* (2013.01);
(Continued)

(58) Field of Classification Search
CPC .................................... B09C 1/00; B09C 1/06
See application file for complete search history.

(56) References Cited

U.S. PATENT DOCUMENTS 4,966,493 A * 10/1990 Rebhan ................... E02D 19/14
                                                                  405/128.6
5,324,137 A     6/1994 Dash
(Continued)

FOREIGN PATENT DOCUMENTS

| CN | 1575376 | 2/2005 |
|---|---|---|
| CN | 106216381 | 12/2016 |

(Continued)

OTHER PUBLICATIONS

"International Search Report (Form PCT/ISA/210) of PCT/CN2017/114262," dated Feb. 1, 2018, with English translation thereof, pp. 1-9.

*Primary Examiner* — Janine M Kreck
(74) *Attorney, Agent, or Firm* — JCIPRNET

(57) ABSTRACT

Disclosed is a method using an environmental-friendly and artificial freezing technique for sealing and displacement of
(Continued)

a soil pollutant. The method for displacement of the soil pollutant comprises: performing an artificial freezing technique on an area and depth of a surveyed contaminated site to form a sealed frozen wall along the perimeter of the contaminated site, by using the excellent permeation resistance function of the frozen wall to seal the contaminated site and to prevent the pollutant from spreading further; selecting a freezing temperature of −10° C. to −30° C. according to characteristics of the freezing temperature and precipitation rate of the pollutant, by controlling the freezing rate to 1 cm/day to 10 cm/day, and performing freezing displacement of the soil pollutant from outside to inside using a principle of freezing purification, to concentrate the pollutant; and subjecting the remaining high concentration of contaminated soil to chemical treatment.

8 Claims, 3 Drawing Sheets

(51) Int. Cl.
*B09C 1/08* (2006.01)
*F25D 17/02* (2006.01)
*G01N 25/04* (2006.01)

(52) U.S. Cl.
CPC .......... *G01N 25/04* (2013.01); *B09C 2101/00* (2013.01)

(56) References Cited

U.S. PATENT DOCUMENTS 5,667,339 A * 9/1997 Dash .................. B09C 1/00
 405/128.6
5,730,550 A 3/1998 Andersland et al.
6,962,466 B2 * 11/2005 Vinegar .............. B01D 53/002
 405/128.4

FOREIGN PATENT DOCUMENTS

| | | |
|---|---|---|
| CN | 106734133 | 5/2017 |
| JP | 2005270963 | 10/2005 |
| JP | 2006082008 | 3/2006 |
| JP | 3814716 | 8/2006 |
| WO | 03035987 | 5/2003 |

* cited by examiner

METHOD USING ARTIFICIAL FREEZING TECHNIQUE FOR SEALING AND DISPLACEMENT OF SOIL POLLUTANT

CROSS-REFERENCE TO RELATED APPLICATION

This application is a 371 of international application of PCT application serial no. PCT/CN2017/114262, filed on Dec. 1, 2017, which claims the priority benefit of China application no. 201710008526.8, filed on Jan. 5, 2017. The entirety of each of the above-mentioned patent applications is hereby incorporated by reference herein and made a part of this specification.

BACKGROUND OF THE INVENTION

1. Technical Field

The present invention relates to an environment-friendly method for treating contaminated soil, and in particular, to a method using an artificial freezing technique for sealing and displacement of a soil pollutant.

2. Background Art

Due to the continuous expansion of the urban area, chemical plants originally located in the suburbs are gradually included in the urban range. To avoid pollution, these chemical plants are moved out, which increases the space for urban development, and also leaves a large number of contaminated sites. To remedy the contaminated sites, a method commonly used at present is using a chemical reaction technique to inject reactive chemical substances into the contaminated sites, or to mix the chemical substances with contaminated soil. Such a method has the following two problems: (1) The injected chemical substances are likely to incur secondary pollution (uneven spreading of the contamination leads to secondary pollution on some uncontaminated soil during the remediation) on the sites; and (2) the contaminated site is tremendous in area and the workload of thorough treatment is rather heavy. For example, for a contaminated site having an area of 4 square kilometers and a depth of 10 m, contaminated soil to be treated reaches 40 million cubic meters according to calculation.

Thus, there is an urgent need to provide a method which can effectively remedy contaminated soil and also avoid secondary pollution.

SUMMARY OF THE INVENTION

Technical Problem: In view of the problems in the existing contaminated soil treatment technique that contaminated soil cannot be effectively remedied and secondary pollution is caused, the present invention provides a method using an artificial freezing technique for sealing and displacement of a soil pollutant.

Technical Solution: The method using an artificial freezing technique for sealing and displacement of a soil pollutant according to the present invention includes: performing, on an area and depth of a surveyed contaminated site, an artificial freezing technique to form a sealed frozen wall along the perimeter of the contaminated site, and using the excellent permeation resistance function of the frozen wall to seal the contaminated site and prevent the pollutant from spreading further; then selecting, on the basis of the freezing temperature and precipitation rate of the pollutant, a freezing temperature of $-10°$ C. to $-30°$ C., controlling the freezing rate to 1-10 cm/day, and using a principle of freezing purification to achieve freezing displacement of the soil pollutant from the perimeter to the center of the site to concentrate the pollutant; and subjecting the remaining highly concentrated contaminated soil to chemical treatment.

Further, drilling positions for artificial freezing are determined according to the area and depth of the surveyed contaminated site, where a drilled freezing hole is 2 m to 6 m distant from the contaminated site and 3 m to 10 m deeper than the contaminated site, or the freezing hole goes deep into the stable aquiclude layer by a distance of 3 m or above. Spacing between the freezing holes is specifically set to 1 m to 3 m according to hydrogeological conditions of the site, and a form of the frozen wall is determined according to the shape of the contaminated site. A closed frozen curtain is formed around the contaminated site.

Further, the type of contamination in the contaminated site is determined and the precipitation characteristics of the pollutant are defined. A freezing precipitation experiment is conducted in a laboratory to determine freezing parameters: the freezing temperature and freezing rate, so as to achieve the most efficient freezing displacement.

Further, an artificial freezing manner uses an ammonia refrigeration system and a brine circulation system. Power of the refrigeration system is determined jointly according to the volume of the frozen soil, ground temperature, air temperature, freezing temperature, and a freezing front advancement rate. A freezing pipe is formed by welding seamless steel tubes, and a liquid supply pipe is a plastic pipe.

Further, for the ammonia refrigeration system, brine circulation in the brine circulation system is normal circulation. After closure of a frozen wall, an internal freezing front advances inwards. With the advancement of the internal freezing front, the freezing pipes are gradually arranged inwards; a region on which displacement is completed is determined, and the freezing pipes in this region are pulled out and are allowed to thaw naturally; the advancement of the freezing front is monitored by using set temperature measurement points. During monitoring of the advancement of the freezing front by using the set temperature measurement points, when the freezing front moves forward 2 m or above, freezing holes are added at the inner side of the frozen wall, where a distance from the freezing hole to the internal freezing front is not less than 0.5 m. The freezing holes at the outer side is allowed to stop freezing and thaw naturally. An alternate advancement mode is adopted.

Further, during freezing displacement, the pollutant content in the frozen soil is measured in real time, and a displacement effect is monitored, to adjust and optimize the freezing parameters and speed up freezing.

Further, the contamination is concentrated in a small closed region by means of freezing displacement, and remaining contaminated soil is subjected to the traditional chemical treatment for pollutants, where a frozen state is maintained during the treatment to prevent secondary leakage of the pollutant due to improper treatment.

Further, when it is determined that the remaining contaminated site reaches the treatment standard, freezing is stopped and the frozen wall is allowed to thaw naturally.

Advantageous Effect: the advantageous effects are as follows: The foregoing solution utilizes a freezing purification function of artificial freezing when liquid water freezes into ice to achieve precipitation of a pollutant, and uses an environment-friendly artificial freezing technique, to only reduce the temperature inside the contaminated site. Thus, the contaminated site can be sealed, and further displacement of the pollutant in the contaminated soil can be achieved in an experimentally validated freezing manner, thus dispensing with a high-cost direct chemical treatment and avoiding a risk of secondary pollution.

The frozen soil curtain for artificial freezing can be flexibly arranged according to the characteristics of the contaminated site. Because the city contaminated site has a depth in a small range, the current drilling precision of the freezing holes can satisfy the requirements for arrangement of the frozen curtain.

The temperature and pollutant concentration are measured in real time during freezing displacement, to further adjust and optimize the freezing parameters: the freezing temperature and freezing rate, and to ensure that the pollutant displacement meets the requirements.

DESCRIPTION OF THE NUMERALS

Figure 1A:
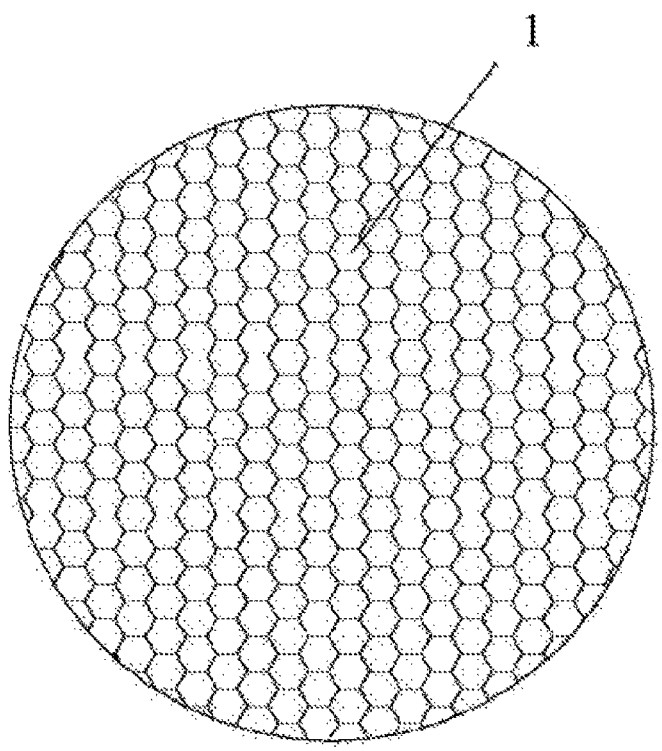
FIG. 1(a) is a schematic diagram of a contaminated site to be treated by using an artificial freezing technique of the present invention.

1. Contaminated site; 2. Internal freezing front; 3. External freezing front; 4. Frozen soil curtain; 5. Freezing pipe; 6. Liquid return pipe; 7. Liquid supply pipe; and 8. Outer part of the freezing pipe

DETAILED DESCRIPTION OF THE INVENTION

The method using an artificial freezing technique for sealing and displacement of a soil pollutant according to the present invention includes: performing, on an area and depth of a surveyed contaminated site, an artificial freezing technique to form a sealed frozen wall along the perimeter of the contaminated site, and using the excellent permeation resistance function of the frozen wall to seal the contaminated site and prevent the pollutant from spreading further; then selecting, on the basis of the freezing temperature and precipitation rate of the pollutant, a freezing temperature of −10° C. to −30° C., controlling the freezing rate to 1 cm/day to 10 cm/day, and using a principle of freezing purification to achieve freezing displacement of the soil pollutant from the perimeter to the center of the site to concentrate the pollutant; and subjecting the remaining highly concentrated contaminated soil to chemical treatment.

Drilling positions for artificial freezing are determined according to the area and depth of the surveyed contaminated site, where a drilled freezing hole is 2 m to 6 m distant from the contaminated site and 3 m to 10 m deeper than the contaminated site, or the freezing hole goes deep into the stable aquiclude layer by a distance of 3 m or above. Spacing between the freezing holes is specifically set to 1 m to 3 m according to hydrogeological conditions of the site, and a form of the frozen wall is determined according to the shape of the contaminated site. A closed frozen curtain is formed around the contaminated site.

The type of contamination in the contaminated site is determined and the precipitation characteristics of the pollutant are defined. A freezing precipitation experiment is conducted in a laboratory to determine freezing parameters: the freezing temperature and freezing rate, so as to achieve the most efficient freezing displacement.

An artificial freezing manner uses an ammonia refrigeration system and a brine circulation system. Power of the refrigeration system is determined jointly according to the volume of the frozen soil, ground temperature, air temperature, freezing temperature, and a freezing front advancement rate. A freezing pipe is formed by welding seamless steel tubes, and a liquid supply pipe is a plastic pipe.

For the ammonia refrigeration system, brine circulation in the brine circulation system is normal circulation. After closure of a frozen wall, an internal freezing front advances inwards. With the advancement of the internal freezing front, the freezing pipes are gradually arranged inwards. A region on which displacement is completed is determined, and the freezing pipes in this region are pulled out and are allowed to thaw naturally. Then, the advancement of the freezing front is monitored by using set temperature measurement points. During monitoring of the advancement of the freezing front by using the set temperature measurement points, when the freezing front moves forward 2 m or above, freezing holes are added at the inner side of the frozen wall, where a distance from the freezing hole to the internal freezing front is not less than 0.5 m. The freezing holes at the outer side are allowed to stop freezing and thaw naturally. An alternate advancement mode is adopted. The brine circulation uses a normal circulation mode where low-temperature brine enters via the liquid supply pipe and returns back via a liquid return pipe.

During freezing displacement, the pollutant content in the frozen soil is measured in real time, and a displacement effect is monitored, to adjust and optimize the freezing parameters and speed up freezing.

The contamination is concentrated in a small closed region by means of freezing displacement, and remaining contaminated soil is subjected to the traditional chemical treatment for pollutants, where a frozen state is maintained during the treatment to prevent secondary leakage of the pollutant due to improper treatment.

When it is determined that the remaining contaminated site reaches the processing standard, freezing is stopped and the frozen wall is allowed to thaw naturally.

The present invention is further described below with reference to the embodiment shown in the accompanying drawings.

Embodiment 1

Figure 1B:
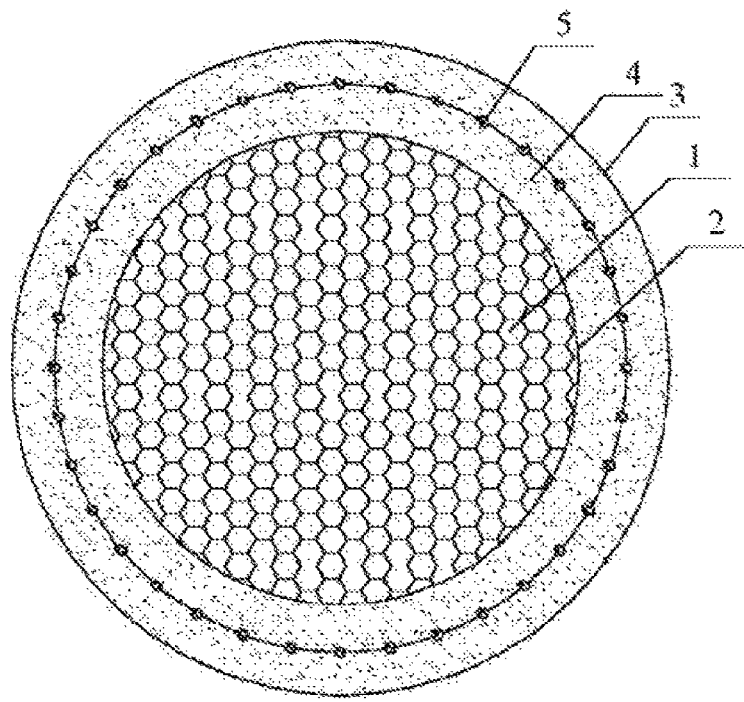
FIG. 1(b) is a schematic diagram of sealing the contaminated site by one-circle arrangement in an artificial freezing technique of the present invention.
Figure 1C:
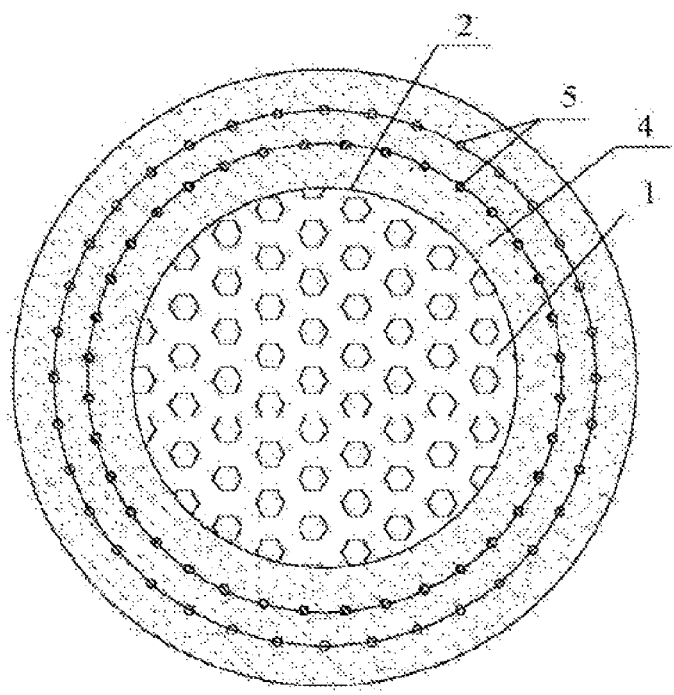
FIG. 1(c) is a schematic diagram of sealing and displacement on the contaminated site by two-circle arrangement in an artificial freezing technique of the present invention.
Figure 1D:
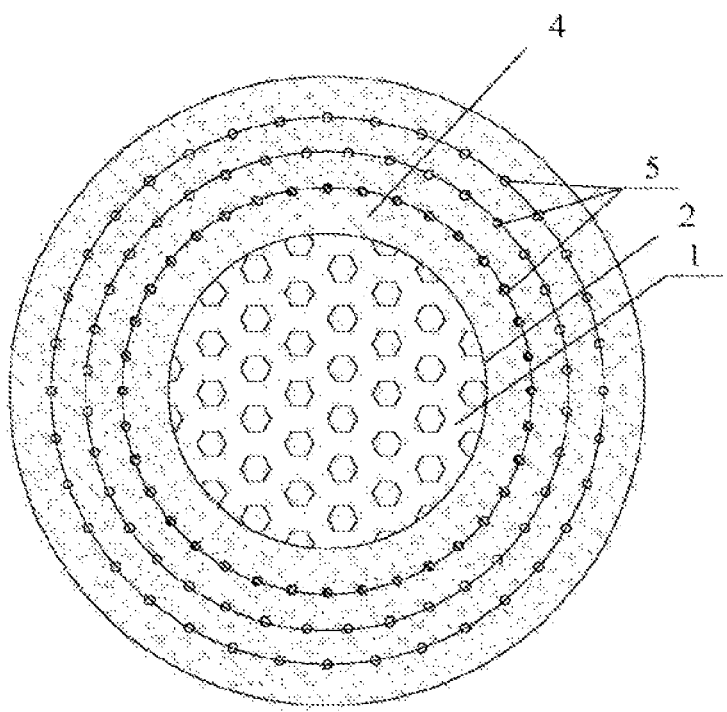
FIG. 1(d) is a schematic diagram of sealing and displacement on the contaminated site by three-circle arrangement in an artificial freezing technique of the present invention.

As shown in FIGS. 1(a) and 1(b), in an artificial freezing technique for sealing and displacement of a soil pollutant, first, according to the characteristics: area and depth, of a contaminated site 1, working freezing pipes are arranged in at least one circle around the contaminated site and 2 m to 6 m distant from the site. FIGS. 1(c) and 1(d) show that the freezing pipes are arranged in two and three circles respectively. The circles formed by the freezing pipes are 1.5 m to 2.0 m apart from each other, and the freezing pipes in each circle are spaced at a distance of 1 m to 3 m. The freezing pipes in adjacent circles are staggered, and each freezing pipe is 3 m to 10 m deeper than the contaminated site.

Figure 2:
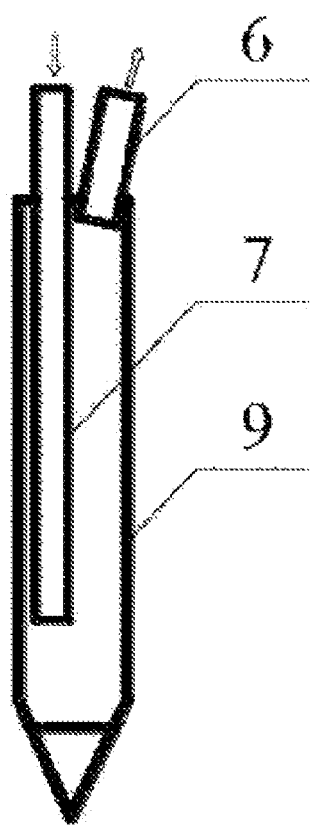
FIG. 2 is a schematic diagram of a freezing pipe of the present invention.

An artificial refrigeration manner is used: ammonia refrigeration is implemented and direct brine circulation is achieved in the working freezing pipes 5. As shown in FIG. 2, low-temperature brine enters via a liquid supply pipe 8 and returns back via a liquid return pipe 7. The outer part 9 of the freezing pipe directly contacts the soil. After closure of a frozen curtain 4, an internal front 2 of a frozen wall and an external front 3 of the frozen wall are monitored in real time by using preset temperature measurement points.

When the internal front of the frozen wall moves towards the contaminated site by 2 m or above, inner-circle freezing pipes 5 are scattered at the inner side of the frozen curtain 4; and outer-circle freezing pipes 5 are allowed to gradually stop freezing, and thaw naturally after a displacement effect is ensured.

To achieve an optimal displacement effect, it is required to carry out an indoor experiment regarding appropriate freezing parameters on the basis of contamination characteristics, so as to determine the freezing temperature and precipitation rate of the pollutant, and the freezing rate. In addition, the freezing parameters: the freezing temperature and freezing rate are adjusted and optimized according to an on-site test for the displacement effect.

After the size of the contaminated site 1 is reduced to a certain range by use of the artificial freezing technique, the diameter of the site ranges from 10 m to 20 m, and the concentration of the pollutant is 150% to 200% higher than that without displacement. In the case that the frozen curtain 4 is maintained, the concentrated soil within the contaminated site is subjected to a chemical treatment. If it is determined through a test that the pollutant within the site reaches the standard, all the freezing pipes 5 are allowed to stop freezing and thaw naturally.

Steps of the method using an artificial freezing technique for sealing and displacement of a soil pollutant of the present invention are summarized as follows:

1. The area and depth of a contaminated site are surveyed and measured in advance; and an arrangement manner of an artificial freezing curtain, including arrangement positions and depth of freezing pipes, is determined according to the characteristics of the contaminated site.

2. The type of the pollutant is determined; and the precipitation rate of the pollutant and the freezing parameters: the freezing temperature and freezing rate are determined based on an experiment.

3. Freezing is carried out by using an ammonia refrigeration system and a brine normal circulation mode, where the freezing pipe is formed by welding seamless steel tubes, and a liquid supply pipe is a plastic pipe.

4. After closure of a frozen wall, an internal freezing front advances inwards to achieve pollutant displacement. Freezing holes are added at the inner side of the frozen wall, and freezing holes at the outer side are allowed to stop freezing and thaw naturally. An alternate advancement mode is adopted.

5. During freezing displacement, the pollutant content in the frozen soil is measured in real time, to adjust and optimize the freezing parameters.

6. The pollutant-concentrated contaminated site after displacement is subjected to a traditional chemical treatment, and a frozen state is maintained during the treatment to prevent secondary leakage of the pollutant.

7. When it is determined that the remaining contaminated site reaches the treatment standard, freezing is stopped and the frozen wall is allowed to thaw naturally.

What is claimed is:

1. A method of using an artificial freezing technique for sealing and displacement of soil pollutant, comprising:
   performing an artificial freezing technique on an area and depth of a surveyed contaminated site to form a sealed frozen wall along a perimeter of the contaminated site, by using an excellent permeation resistance function of the frozen wall to seal the contaminated site to prevent the soil pollutant from spreading further;
   selecting a freezing temperature of −10° C. to −30° C. according to characteristics of a freezing temperature and a precipitation rate of the soil pollutant, by controlling a freezing rate to 1 cm/day to 10 cm/day, performing freezing displacement of the soil pollutant from the perimeter of the contaminated site to a center of the contaminated site using a principle of freezing purification, to concentrate the soil pollutant; and
   subjecting a remaining high concentration of contaminated soil to a chemical treatment.

2. The method of using the artificial freezing technique for sealing and displacement of soil pollutant according to claim 1, further comprising
   determining a drilling position for an artificial freezing according to the area and depth of the surveyed contaminated site, a drilled freezing hole is 2 m to 6 m away from the contaminated site and 3 m to 10 m deeper than the depth of the contaminated site, or the freezing hole goes deep into an aquiclude layer by a distance of 3 m and above;
   determining a spacing between the freezing holes which is specifically set to 1 m to 3 m according to hydrogeological conditions of the contaminated site, and
   determining a form of the frozen wall according to a shape of the contaminated site; and
   forming a closed frozen curtain around the contaminated site.

3. The method of using the artificial freezing technique for sealing and displacement of soil pollutant according to claim 1, further comprising
   determining a type of contamination in the contaminated site and defining a precipitation characteristics of the soil pollutant;
   conducting a freezing precipitation experiment in a laboratory to determine freezing parameters: the freezing temperature and a freezing rate for the freezing displacement.

4. The method of using the artificial freezing technique for sealing and displacement of soil pollutant according to claim 1, wherein the artificial freezing technique uses an ammonia refrigeration system and a brine circulation system; a power of the ammonia refrigeration system is jointly determined according to a volume of a frozen soil, a ground temperature, an air temperature, a freezing temperature, and a freezing front advancement rate; and a freezing pipe is formed by welding seamless steel tubes, and a liquid supply pipe is a plastic pipe.

5. The method of using the artificial freezing technique for sealing and displacement of soil pollutant according to claim 4, wherein for the ammonia refrigeration system, a brine circulation in the brine circulation system is a normal circulation; after a closure of the frozen wall, an internal freezing front advances inwards; with the advancement of the internal freezing front, the freezing pipes are gradually arranged inwards; a region on which displacement is completed is determined, and the freezing pipes in the region are pulled out and are allowed to thaw naturally; the advancement of the internal freezing front is monitored by using set temperature measurement points; during monitoring of the advancement of the internal freezing front by using the set temperature measurement points, when the freezing front moves forward for 2 m and above, freezing holes are added at an inner side of the frozen wall, wherein a distance from the added freezing holes to the internal freezing front is not less than 0.5 m; the freezing holes at an outer side of the frozen wall are allowed to stop freezing and thaw naturally, wherein during the normal circulation, a low-temperature brine enters the freezing pipes via a liquid supply pipe and returns back via a liquid return pipe.

6. The method of using the artificial freezing technique for sealing and displacement of soil pollutant according to claim 1, wherein during the freezing displacement, a content of the soil pollutant in a frozen soil is measured in real time, and a displacement effect is monitored, to adjust and to optimize freezing parameters, and to speed up the freezing displacement.

7. The method of using the artificial freezing technique for sealing and displacement of soil pollutant according to claim 1, wherein the contaminated soil is concentrated in a small closed region by means of the freezing displacement, and the remaining contaminated soil is subjected to the chemical treatment for the soil pollutant, wherein a frozen state is maintained during the chemical treatment to prevent secondary leakage of the soil pollutant due to improper treatment.

8. The method of using the artificial freezing technique for sealing and displacement of soil pollutant according to claim 1, wherein after determining the remaining contaminated site reaches a processing standard, the artificial freezing technique is stopped and the frozen wall is allowed to thaw naturally.

* * * * *